United States Patent [19]

Linehan

[11] 4,072,152
[45] Feb. 7, 1978

[54] ORTHOPEDIC CRYOSURGICAL APPARATUS

[76] Inventor: John H. Linehan, 6028 N. Santa Monica Blvd., Whitefish Bay, Wis. 53217

[21] Appl. No.: 660,157

[22] Filed: Feb. 23, 1976

[51] Int. Cl.² ............................................ A61B 17/36
[52] U.S. Cl. .................................. 128/303.1; 128/402
[58] Field of Search ............... 62/293; 128/303.1, 400, 128/402

[56] References Cited

U.S. PATENT DOCUMENTS

| 2,429,238 | 10/1947 | Restarski et al. | 128/400 |
| 3,421,508 | 1/1969 | Nestrock | 128/303.1 |
| 3,467,104 | 9/1969 | Burbridge et al. | 128/400 |
| 3,674,031 | 7/1972 | Weiche | 128/303.1 |
| 3,823,718 | 7/1974 | Tromovitch | 128/303.1 |
| 3,916,911 | 11/1975 | Sauder et al. | 128/400 |
| 3,948,269 | 4/1976 | Zimmer | 128/303.1 |

*Primary Examiner*—Stephen C. Pellegrino
*Assistant Examiner*—Michael H. Thaler
*Attorney, Agent, or Firm*—Andrus, Sceales, Starke & Sawall

[57] ABSTRACT

Apparatus for performing cryosurgical procedures on bone tumors includes a source of liquid nitrogen. Generally U-shaped probes formed of lead are connected to the source and placed on the exposed surface of the tumor. The liquid nitrogen is passed through the probe to produce necrosis of the tumor. Temperatures are monitored by temperature indicating means.

8 Claims, 2 Drawing Figures

ORTHOPEDIC CRYOSURGICAL APPARATUS

BACKGROUND OF THE INVENTION

1. Field of the Invention

The present invention relates to sugical instruments for providing cryogenic temperatures.

2. Description of the Prior Art

Extremely cold temperatures may be used to destroy tissue for therapeutic purposes. This technique, commonly called "cryosurgery", has proven highly useful in the treatment of certain conditions that cannot be dealt with by the conventional surgical techniques of incision and excision. For example, small areas in the interior of the brain may be destroyed by cryosurgery in the treatment of Parkinson's disease. A needle-like probe is inserted in the brain to the desired location and filled with a cryogen to produce necrosis. The cryogen most often used is liquid nitrogen because of its low temperature (boiling point -196° C, −321° F), non-toxicity, and economy.

More recently, cryosurgery has been used to treat orthopedic conditions, for example, cancerous bone conditions or bone tumors which are many orders of magnitude larger than the brain areas noted above. An early orthopedic procedure involved exposing and removing the tumor by conventonal procedures and thereafter simply pouring liquid nitrogen directly into the cavity to kill the remaining abnormal cells.

While this procedure is resonably effective, it is difficult to control the size of the area which is frozen, to insure killing temperatures are reached, and to prevent injury to surrounding healthy tissues. A reproducible, controllable temperature curve cannot be obtained. To avoid these shortcomings, a conduit-like probe has been applied to the bone through which the liquid nitrogen is circulated to effect the freeze.

It will be appreciated that the conduit must be bent and shaped to closely conform to the tumor or bone area in order to achieve good heat transfer and freezing of the target area. In the past, copper has been used as the material for the probe because of its high thermal conductivity. Unfortunately, copper materials having the structrual strength necessary for cryosurgical applications are so stiff that tools are necessary to bend the probe. Forming the probe from tubing tended to work harden the material making it even more difficult to bend. The surgeon must consult x-rays to ascertain the size and shape of the tumor. In preparation for the surgery, the probe is hammered or bent with pliers into a configuration which conforms to the shape the tumor is believed to occupy.

Often, however, the size and shape of the tumor once exposed, differs from that indicated by the two dimensional x-rays so that the probe does not achieve a good heat transfer relationship with the tumor, making it difficult to rapidly and adequately carry out the operation. The shape of the probe cannot be easily altered because of the need for tools and the risk of rupture or collapse of the probe.

The poor heat transfer arises because of the presences of air pockets between the inappropriately formed probe and the tumor. Inasmuch as the thermal conductivity of air is 1/15,000th that of copper, the presence of even small air pockets is highly detrimental to heat transfer.

It is also necessary to closely control the feed rate of the liquid cryogen to obtain the desired temperature and to reduce operating time. In the past, a resistance heater has been employed in conjunction with the cryogen reservoir to boil a portion of the cryogen into the gaseous form to pressurize the flask and propel the cryogen through the probe. However, starting the cryogen flow produced in this manner is difficult because of the time lag between the energization of the resistance heater and creation of the gas pressure necessary to propel the cryogen. It is difficult to control, and particularly to vary, flow rates with such a technique. It may also needlessly prolong the operative procedure.

SUMMARY OF THE PRESENT INVENTION

The cryosurgical apparatus of the present invention includes a probe which is sufficiently flexible to permit bending by the surgeon at the operating table, thereby insuring that the configuration of the probe will closely match the area to be treated. Such a probe may be formed of lead. Lead has a thermal conductivity an order of magnitude less than that of copper. However, the flexibility of lead permits such precise shaping of the probe that air pockets between the probe and the tumor are substantially obliterated. This advantage more than offsets the lower thermal conductivity of lead. The cryosurgical apparatus of the present invention also includes a means for instantaneously starting and closely controlling the flow of the liquid cryogen to the probe so as to insure precise temperature control and to reduce wastage of the cryogen.

In summary, the present invention includes a source of liquid cryogen, such as Dewar flask. The inlet port of a probe, comprised of a generally U-shaped lead conduit, is connected to the flask by a supply tube. A discharge tube is connected to the outlet port of the probe for discharging the cryogen. A source of gas pressure is coupled to the flask for instantaneously and precisely controlling the flow of cryogen through the supply and discharge tubes and one or more of the probes. Temperature obtaining and indicating means are provided for monitoring the temperature obtained by the application of the probe to the tumor.

DETAILED DESCRIPTION OF THE PREFERRED EMBODIMENT

Figure 1:
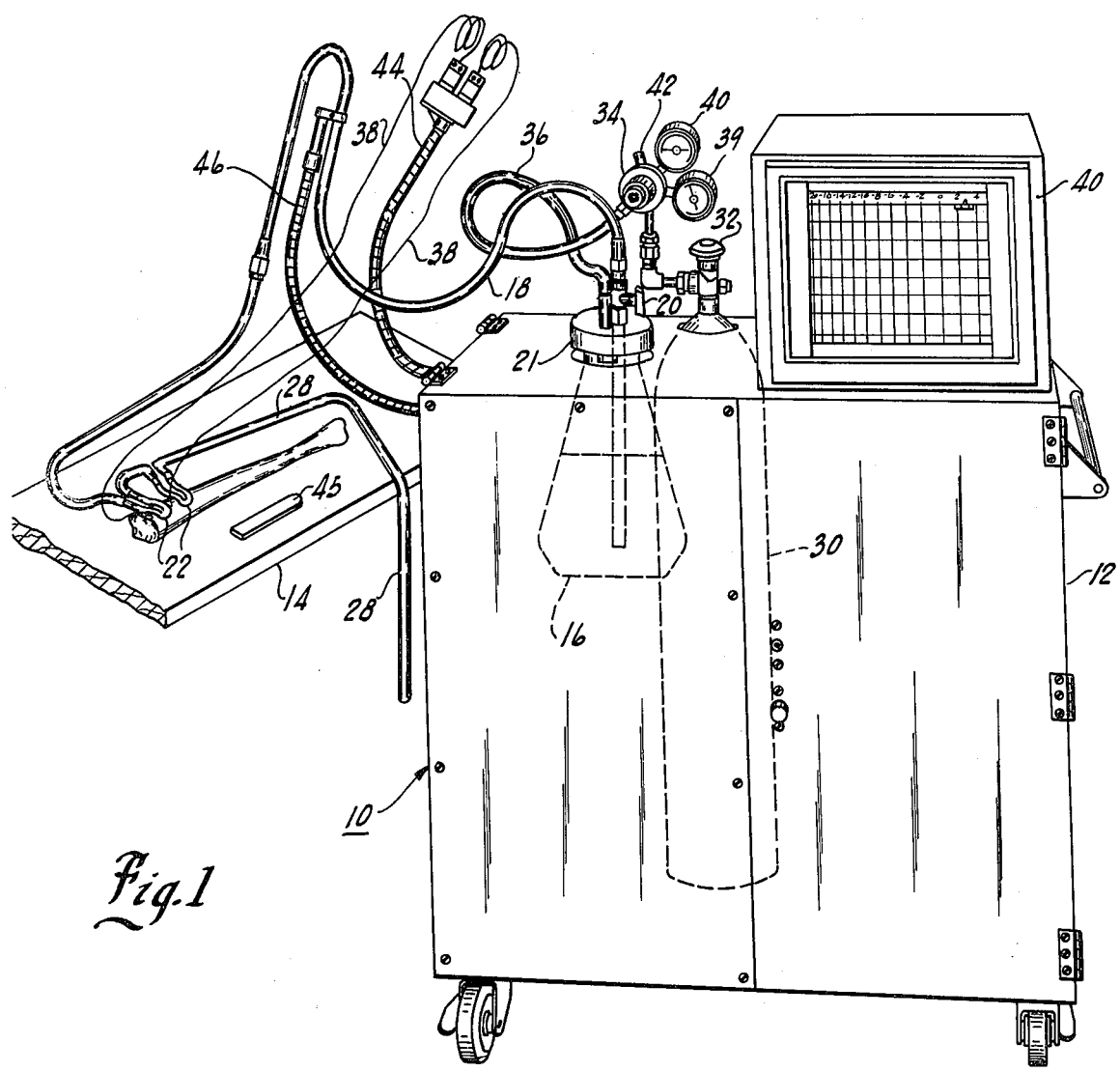
FIG. 1 is a schematic diagram of the cryosurgical apparatus of the present invention.

Turning now to FIG. 1 there is shown therein the cryosurgical apparatus of the invention indicated by the numeral 10. Certain portions of the apparatus may be mounted in a cart 12 which may be rolled to the side of the operating table 14.

Apparatus 10 includes a source of a liquid cryogen, typically liquid nitrogen. This source may be a Dewar bottle or flask 16 having an evacuated space between two highly reflective walls which keeps the liquid nitrogen below its boiling point.

Figure 2:
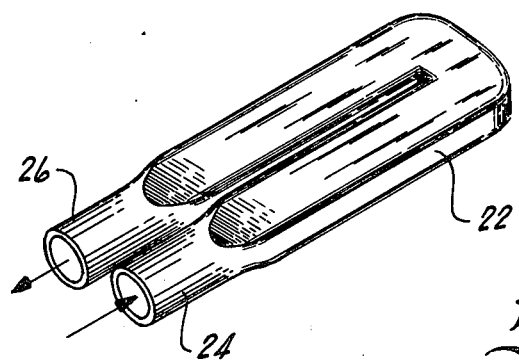
FIG. 2 is an enlarged perspective view of the probe element of the cryosurgical apparatus which applies the freezing temperatures to the bone area to be treated.

A supply tube 18, the initial portions of which may be formed of a braid reinforced tetrafluoroethylene hose and the terminal portion is formed of a rubber tube, leads from flask 16 through an/off valve 20 in cap 21 of flask 16 to one or more cryoprobes 22, shown in detail in FIG. 2.

Cryoprobe 22 may be generally U-shaped hollow tube having a pair of parallel, closely spaced arms and an intermediate, bent joinder section forming a flow passage for the liquid cryogen. An inlet 24 on one arm of the U-shpaed tube is connected to supply tube 18 and an outlet 26 on the other arm is connected to discharge tube 28. Discharge tube 28 usually opens into the atmosphere.

The size of cryoprobe 22 depends on the size of the area to be treated. Cryoprobe 22 is typically 2 to 4 inches long and 1 to 1½ inches wide. The probe may be formed of tubing which is flattened to a generally rectangular form so as to present as large a contact surface with the area to be treated as possible. The thickness of the tubing wall may be 0.0625 inch and the cross sectional area of the flow passage may be 0.035 square inches. Inlet 24 and outlet 26 may remain rounded, as shown in FIG. 2, to mate with supply tube 18 and discharge tube 28.

It is necessary that cryoprobe 22 be formed of a material capable of resisting the thermal and mechanical stresses to which the cryoprobe is subjected. It is particularly desirable that the probe be formed of a material which can be easily deformed, preferably by hand. This enables the surgeon to bend the probe to the desired configuration at the operating table, once the size and shape of the tumor to be treated has been ascertained by visual inspection after incision.

For the reasons noted supra, in the preferred embodiment of the invention, probe 22 is formed of lead. In addition to its flexibility, lead is sufficiently inexpensive that the probe may be disposed of after use.

The liquid nitrogen is caused to flow through supply tube 18, cryoprobe 22, and discharge tube 28 by the pressure of gaseous nitrogen applied to the exposed surface of the liquid nitrogen in Dewar flask 16. For this purpose, a cylinder 30 of gaseous nitrogen is provided and connected through valve 32, pressure reducer 34, and tubing 36 to Dewar flask 16. The pressure levels generated in Dewar flask 16 by the gaseous nitrogen of cylinder 30 are utilized to control the flow rates of liquid nitrogen through cryoprobe 22. The pressure levels are ascertained by gages 39 and 40 which monitor the cylinder and flask pressures, respectively. Pressure reducer 34 also contains safety valve 42 which prevents build up of excessive pressures in flask 16.

The cryogenic temperatures generated by apparatus 10 are sensed by thermocouples 38 which are applied to the area to be frozen. The thermocouples 38 are connected to chart recorder 40 to indicate the temperatures obtained during the cryosurgery.

In an operation, an incision is made to approach the area, such as the bone lesion or tumor, to be subjected to cryosurgery. The adjacent tissues are dissected and retracted away from the bone. This is preferably done with the plastic retractors 45 shown in FIG. 1 which are manipulated by the surgeon to both hold the tissue away from the area of surgery and act as thermal insulators to the surrounding tissue to prevent injury to soft tissue.

Thermocouples 38 are placed about the periphery of the target area of surgery. In the case of a bone tumor this may be accomplished by drilling holes in the bone to receive the thermocouples. The exact locations of the temperature sensing elements of the thermocouples are determined and recorded by x-ray.

The thermocouples preferably comprise fine wires in a stainless steel sheath. The sheath facilitates insertion in the bone, due to its rigidity and provides good delineation in x-rays. The fine thermocouple wires contained within the sheath minimize temperature measuring errors due to unwanted cooling of the thermocouple junction in the event the thermocouple is in near proximity of a cryoprobe.

Sterilized, malleable cryoprobes 22 are shaped by hand to conform to the lesion.

Typically a plurality of cryoprobes such as the pair shown in FIG. 1 are used during an operation. The cryoprobes are connected in series and/or parallel between supply tube 18 and discharge tube 28. As many as six probes have been used.

The close contouring of cryoprobes 22 tends to eliminate air pockets between the probes and the tumor which act as insulators. Heat transfer may be further improved by further reducing the remaining few air spaces between probes 22 and the tumor by filling them with a liquid, or other heat conductor. Saline soaked cellulose sponges may be used for this purpose. Probes 22 may be retained on the surface to be frozen by wiring them to the bone. Goosenecks 44 and 46 position thermocouples 38 and supply line 18 above the surgical field.

Valve 32 is then opened to provide pressure in Dewar flask 16 through tubing 36. Valve 20 is opened so that liquid nitrogen flows through tubing 18 to cryoprobes 22. The cryogenic temperatures generated in probes 22 freeze the contacting portions of the tumor or lesion. Temperatures of between $-20°$ C and $-60°$ C are required to produce necrosis. The temperatures generated in the tumor are sensed by thermocouples and monitored on recorder 40.

The flow rate of the liquid nitrogen through cryoprobe 22 is adjusted by varying the gas pressure inside flask 16 by regulator 34 so that nucleate boiling of the liquid nitrogen occurs in the cryoprobes 22. Such nucleate boiling utilizes the latent heat of vaporization of liquid nitrogen to cool the lesion. This type of heat transfer may be effectively monitored by observing the opening of discharge tube 28 to insure that an amount of liquid nitrogen sufficient to wet the operating table drape exits discharge tube 28. It is important to utilize nucleate boiling to insure a maximum boiling thermal conductance in the liquid nitrogen in cryoprobes 22. The liquid nitrogen flow rate will usually vary from freeze to freeze depending on the number of probes utilized and will generally be greater at the beginning of the freeze than at the end. Typically 1 to 10 liters of liquid nitrogen are utilized during a surgical procedure.

The freezing time depends on the flow rate of the liquid nitrogen, the number of probes used, the probe surface area and degree of contact, the mass to be frozen and the number of previous freezes. It is desirable to freeze as rapidly as possible. Freeze times of 5 to 30 minutes are typical with the apparatus of the present invention due to the conformability of the probe and the nucleate boiling of the cryogen. At the conclusion of the freeze valves 20 and 32 are closed and flask 16 is depressurized immediately terminating the flow of the liquid nitrogen.

A slow thaw favors more complete tissue death. Usually the thawing time is twice as long as the freezing time. Once the lesion and the apparatus have warmed to the freezing point, the thermocouples and cryoprobes may be removed from the lesion. Or, a second freeze may be performed.

In some procedures the tumor may be curretted and the cavity thus created filled with saline soaked sponges and a probe or probes placed inside the cavity for a second freeze of the cavity walls. The second freeze, if performed, is usually accomplished more quickly than the first.

Post operative procedures, ultimately resulting in a closure of the wound, are undertaken after thawing of the freeze and removal of the thermocouples and probes.

Various modes of carrying out the invention are contemplated as being within the scope of the following claims particularly pointing out and distinctly claiming the subject matter which is regarded as the invention.

I claim:

1. Apparatus for performing cryosurgical procedures on bone tumors comprising:
   a source of a cryogenic liquid;
   probe means comprising a deformable U-shaped conduit having a pair of parallel, close-spaced arms and an intermediate bent joinder section, one of said arms having an inlet port on the end thereof, the other of said arms having an outlet port on the end thereof, said arms and joinder section having a uniform rectangular cross-sectional configuration along substantially their entire length between said ports, said rectangular cross-section having a minor dimension parallel to the axis of bending of said joinder section and a major dimension normal thereto, said probe means having a pair of U-shaped flattened planar heat transfer surfaces along said major dimension and spaced apart by said minor dimension, said probe means being formed of lead for being capable of gross configuration changes in said U-shaped flattened heat transfer surfaces out of the planar condition through deformation by hand and for retaining such configuration after deformation;
   a supply tube connected to said cryogenic liquid source and to said inlet port of said probe means for supplying the cryogenic liquid through said probe means;
   a discharge tube connected to said outlet port of said probe means for discharging the cryogenic liquid; and
   temperature monitoring means connectable to the bone tumor for monitoring the temperatures obtained in the bone tumor by the application of said probe means.

2. The apparatus according to claim 1 wherein said source of cryogenic liquid includes a flask containing said liquid and gas supply means coupled to said flask for injecting gas in said flask for generating a flow controlling pressure in said flask to supply the cryogenic liquid to said supply tube and for establishing the flow rate of the cryogenic liquid through said conduit and the heat transfer along said flattened surface.

3. The apparatus according to claim 2 wherein said gas supply means is further defined as injecting variable quantities of gas for adjustably pressurizing said flask to control the flow rate of the cryogenic liquid through said probe means.

4. The apparatus according to claim 2 wherein said cryogenic liquid comprises liquid nitrogen and said gas supply means is further defined as comprising means for injecting gaseous nitrogen into said flask.

5. The apparatus according to claim 1 wherein said probe means includes a plurality of U-shaped conduits connected between said supply and discharge tubes.

6. The apparatus according to claim 1 wherein said cryogenic liquid comprises liquid nitrogen.

7. The apparatus according to claim 1 wherein said temperature monitoring means includes a thermocouple means connectable to the tumor and recording means connected to said thermocouple means for indicating temperatures obtained in the tumor.

8. The apparatus according to claim 7 wherein said thermocouple means is further defined as including fine wire thermocouples in a metallic sheath.

* * * * *